(12) United States Patent
van Ophuysen (10) Patent No.: US 8,684,735 B2
(45) Date of Patent: Apr. 1, 2014

(54) ABUTMENT INLAY

(71) Applicant: Straumann Holding AG, Basel (CH)

(72) Inventor: Andreas van Ophuysen, Basel (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 13/690,283

(22) Filed: Nov. 30, 2012

(65) Prior Publication Data

US 2013/0143178 A1 Jun. 6, 2013

(30) Foreign Application Priority Data

Dec. 6, 2011 (EP) .................................... 11009618

(51) Int. Cl.
*A61C 8/00* (2006.01)

(52) U.S. Cl.
USPC ........................................ 433/173; 433/223

(58) Field of Classification Search
USPC ........................................ 433/173, 174, 223
See application file for complete search history.

(56) References Cited

U.S. PATENT DOCUMENTS

| | | | |
|---|---|---|---|
| 5,110,292 A * | 5/1992 | Balfour et al. ................ | 433/173 |
| 5,195,892 A * | 3/1993 | Gersberg ...................... | 433/174 |
| 5,447,435 A | 9/1995 | Brodbeck | |
| 5,685,714 A | 11/1997 | Beaty et al. | |
| 5,688,123 A * | 11/1997 | Meiers et al. ................. | 433/173 |
| 6,227,859 B1 * | 5/2001 | Sutter .......................... | 433/173 |
| 6,332,777 B1 * | 12/2001 | Sutter .......................... | 433/173 |
| 6,461,160 B1 * | 10/2002 | Sutter .......................... | 433/173 |
| 6,726,480 B1 * | 4/2004 | Sutter .......................... | 433/173 |
| 8,113,835 B2 * | 2/2012 | Yau et al. ...................... | 433/173 |
| 2011/0123948 A1 * | 5/2011 | Hinrichsen ................... | 433/173 |

FOREIGN PATENT DOCUMENTS

EP 1269932 A1 1/2003

* cited by examiner

*Primary Examiner* — Ralph Lewis
(74) *Attorney, Agent, or Firm* — Novak Druce Connolly Bove + Quigg LLP (57) ABSTRACT

An inlay for connection to a dental implant, including implant connection geometry, for connecting the inlay to the implant and, coronal of the implant connection geometry, a post portion extending along a longitudinal axis, the post portion having a circular symmetric external surface and including at least one protrusion extending radially beyond said external surface, wherein the post portion further includes longitudinally extending grooves which extend radially inward of said external surface and are located directly adjacent to and on either side of the at least one protrusion such that the proximal end of said at least one protrusion is located radially inward of said external surface. The inlay is used in combination with an overlay including an accommodation cavity for housing the post portion of the inlay, the accommodation cavity having a circular symmetric cavity wall and at least one groove dimensioned such that the one or more protrusion of the inlay can be housed in the one or more groove of the overlay in order to inhibit relative rotation between the components.

22 Claims, 5 Drawing Sheets

ABUTMENT INLAY

CROSS-REFERENCE TO RELATED APPLICATIONS

This application claims priority to European Patent Application No. 11009618.7, filed Dec. 6, 2011, the disclosure of which is incorporated herein by reference in its entirety.

BACKGROUND OF THE INVENTION

This invention relates to an inlay of a dental component, in particular a dental abutment, for use in combination with a dental implant. The component consists of the inlay, which in use connects the component to the implant, and another part for carrying out the main function of the component, for example supporting a dental prosthesis. The two parts are in use fixed together and may be constructed of different materials.

Dental implants are used to replace individual teeth or for anchoring more complex structures, which generally replace several or even all of the teeth. The materials used for dental implants are often titanium and alloys thereof. These materials have the necessary strength for withstanding the mechanical loads that occur, and they are at the same time sufficiently biocompatible for osseointegration and long term use in the mouth.

Implants have two essential parts: an anchoring part and an abutment part. The anchoring part is embedded in the bone, where it osseointegrates with the bone tissue to provide a firm anchor for the prosthesis. The abutment extends into the oral cavity and provides a support for the prosthesis. The desired prosthetic element (e.g. bridge or crown) is fastened over the abutment such that at least part of the abutment is housed within the prosthesis and provides core support to this. The prosthetic element can be adhesively bonded, cemented, screwed or directly veneered onto the abutment.

The implant can be constructed in one part, such that the anchoring part and abutment part are produced in one integral piece. Hence in such implant systems the integrated anchoring part and abutment are always positioned within the mouth at the same time and the single piece implant extends through the soft tissue into the oral cavity to form a core support for the prosthesis.

However, implants are also often constructed in two or more parts, in which case they consist of at least an anchoring component, often referred to in isolation as the implant, and a separate abutment, sometimes referred to as a spacer. The anchoring component is usually either embedded completely in the bone, that is to say to the height of the alveolar crest, or protrudes by a few millimeters from the alveolar crest into the soft tissue. The abutment is mounted either directly or indirectly to the anchoring component after the latter has become incorporated (osseointegrated) into the bone or directly after the anchoring component has been inserted. It can also be attached to the anchoring component prior to insertion. Most usually the abutment is not mounted until after osseointegration. In such cases a component called a healing cap is often mounted to the implant during the osseointegration process to prevent incursion of soft tissue over the implant site.

In contrast to one piece implants, multi-part implants are more versatile, because the anchoring part and the abutment can be adapted to individual requirements. In particular the abutment shape and angulation, relative to the anchoring part, can be selected after implant insertion. This provides the surgeon with more flexibility and room for error in the placement of the implant. An additional advantage of multi-part implants is that the abutment can be made from a different material than the anchoring part.

Due to their versatility multi-part and particularly two-part dental implants are more commonly used than one-piece implants, and it is this form of implant system with which the present invention is concerned. For the remainder of this specification therefore, the term "implant" will be used to denote the anchoring component of a multi-part implant, namely, the element which in use is anchored within the bone but which does not directly provide core support to the final prosthesis, and the term "secondary component" will be used to denote a component which is, in use, directly or indirectly fastened to the implant. The secondary component can be an abutment, which in use extends into the oral cavity and provides core support for a dental prosthesis, and thus forms a part of the complete implant, or in some instances may comprise an auxiliary component which is temporarily fixed to the implant, such as a healing cap.

As mentioned above, one advantage of multi-part implants is that the abutment can be made of a different material than the implant. Although titanium and its alloys possess many qualities that make these materials particularly suited for dental implants, one large disadvantage is their colouring. It is a relatively common occurrence that, after implant placement, some bone absorption (bone loss) occurs, which leads to a corresponding displacement of the gingiva and the exposure of the implant structure, including parts of the abutment. The grey, metallic colour of titanium means that any such exposure is noticeable and unsightly. In addition, when the abutment is made of metal the covering prosthesis must be opaque enough to prevent any metal colouring from showing through the prosthesis, as this will reduce the natural appearance of the restoration.

In recent years there has been much interest in the use of ceramic materials, such as zirconium dioxide and silicon dioxide, for implant structures including both implants and abutments. Ceramics have the necessary strength and biocompatibility needed and in addition have a white colouring which is more aesthetically pleasing. However, ceramic materials are also more brittle than metals, meaning these are harder to manufacture and consequently more expensive. In addition the use of ceramic implants is still a developing field and the long term success of such implants is not yet known.

In order to combine the aesthetic appeal of ceramics with the functionality and established success of titanium implants, so-called hybrid abutments are known.

These consist of a metal inlay, which comprises connection geometry to enable this to be securely and non-rotationally connected to an implant. Coronal of the connection geometry is a post portion to which a ceramic overlay can be attached, via bonding, moulding, sintering etc. The ceramic overlay thus comprises at its apical end an accommodation cavity in which the post portion of the inlay is housed. The overlay is designed such that, in use, this extends through the soft tissue into the oral cavity to provide support for a dental prosthesis. In this way, the connection between the implant and abutment is metal-to-metal, and thus creates a secure attachment which will not deteriorate over time, while the coronal areas of the abutment are ceramic and hence provide an improved visual appearance.

In accordance with conventional dental terminology, "apical" refers to the direction towards the bone and "coronal" to the direction towards the teeth. Therefore the apical end of a component is the end which, in use, is directed towards the jaw bone and the coronal end is that which is directed towards the oral cavity.

Examples of hybrid abutments are known, for example, from U.S. Pat. No. 5,447,435; EP1269932 and U.S. Pat. No. 5,685,714.

In all such hybrid abutments, it is important to ensure that there is no relative rotation between the inlay and overlay once these have been connected together. In many cases this rotational security is achieved by providing complementary anti-rotation means on the inlay post and in the overlay cavity. Such anti-rotation means must be non-circular symmetrical about the longitudinal axis of the post and cavity, which in use are co-axial. Thus, the anti-rotation means may consist of a section of the post portion and accommodation cavity having complementary oval or polygonal cross-sections, e.g. octagonal. When the octagonal post portion is inserted into the octagonal cavity it is not possible to rotate the inlay relative to the overlay. Alternatively the anti-rotation means may comprise one or more radially extending protrusion on either the post portion or cavity which is arranged to fit within a complementary groove on the cavity or post portion respectively.

It is important that the anti-rotation means of the inlay and overlay fit together snugly, both in order to prevent rotational play and also to ensure that there are no gaps at the external interface of the components, which could form bacteria traps. The creation of precisely connecting anti-rotation means, particularly within a brittle ceramic overlay, can be complex and lead to high manufacturing costs.

BRIEF SUMMARY OF THE INVENTION

The object of at least a preferred embodiment of the present invention is to ease the manufacturing process of hybrid abutments and other secondary components as well as to improve the fit between the inlay and overlay.

In addition it is a further object of at least a preferred embodiment of the present invention to provide an inlay which is especially suited to bonding, or cementing, to the overlay.

According to one aspect the present invention provides an inlay for connection to a dental implant, comprising implant connection geometry, for connecting the inlay to the implant and, coronal of the implant connection geometry, a post portion extending along a longitudinal axis, the post portion having a circular symmetric external surface and comprising at least one protrusion extending radially beyond said external surface, wherein the post portion further comprises longitudinally extending grooves which extend radially inward of said external surface and are located directly adjacent to and on either side of the at least one protrusion such that the proximal end of said at least one protrusion is located radially inward of said external surface.

The grooves on either side of the at least one protrusion result in the creation of an "inset" protrusion, that is the proximal end of the protrusion is located within the circumference of the external circular symmetric surface of the post portion. In this way the lateral sides of the protrusion do not extend from the circular symmetric surface but through this.

When protrusions are formed which extend from a circular symmetric or other curved surface using standard machining techniques a sharp, angled transition between the curved outer surface and the protrusion is not possible. Instead the transition occurs over a radius.

This is problematic when it is intended to accommodate the protrusions within complementary grooves formed in a cavity, as in contrast to the manufacturing process for the protrusions, such grooves usually have sharper, more angular transitions between the cavity wall and the grooves. In order to prevent rotational play between the inlay and overlay, the width of the grooves and protrusions must be as closely dimensioned as possible. Thus, differences in the shape of transition at the lateral edges (sides) of the groove and protrusion results in an imprecise fit between the inlay and overlay. The sharp edges of the accommodation cavity can score the curved transition at the edges of the protrusion, leading to chipping of the sharp edges and/or jamming of the overlay on the inlay, which prevents correct seating of the two component parts and can cause an unacceptable level of relative rotation.

The longitudinal grooves of the present invention prevent this problem from occurring. As the grooves are located directly adjacent to the lateral sides of the protrusion(s) there is no curved transition between the circular symmetric surface and these sides of the protrusion(s). Instead the protrusion(s) in effect continues down into the body of the post portion and any curved transition at the lateral edges of the protrusion(s) occurs within the circumference of the circular symmetric surface. Thus, no conflict is caused between these areas of transition and the sharp lateral edges of the overlay.

Figure 1A:
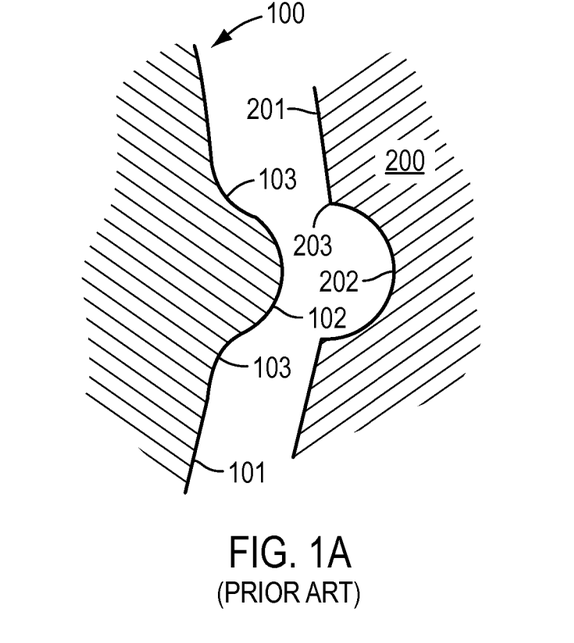
FIG. 1A shows a schematic detail of the anti-rotational connection between a prior art inlay and overlay.
Figure 1B:
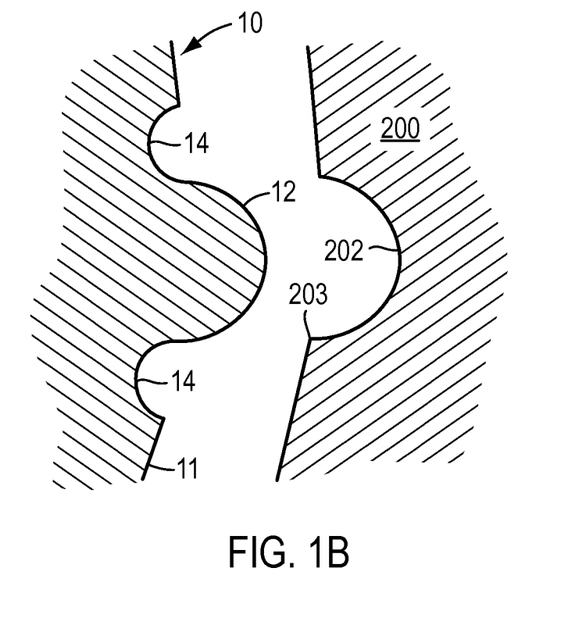
FIG. 1B shows a schematic detail of the anti-rotational connection between an inlay in accordance with the present invention and an overlay.

The advantage provided by the present invention is demonstrated by a comparison of FIGS. 1A and 1B. FIG. 1A shows the prior art anti-rotational connection between an inlay 100 and an overlay 200. The figure shows a partial cross-section through the post portion of the inlay and the cavity of the overlay, taken in a plane perpendicular to the longitudinal axis of the post portion. For clarity the inlay and overlay have been spaced apart. The inlay 100 comprises a circular symmetric external surface 101 from which a protrusion 102 extends. The transition 103 between the outer surface 101 and protrusion 102 is curved. The overlay 200 comprises a circular symmetric cavity wall 201 sized to accommodate the circular symmetric surface 101 of the inlay 100. Groove 202 is cut into the cavity wall 201 and has a shape which complements the protrusion 102 such that the protrusion 102 can be housed within groove 202 to prevent relative rotation between the inlay 100 and overlay 200. However, in contrast to the inlay 100, the transition 203 between the cavity wall 201 and the groove 202 is angular. This leads to the problems discussed above, and increases the angular play between the inlay 100 and overlay 200 as the protrusion is either not fully housed in the groove or the groove must be widened to accommodate the transition 103 and thus not snugly house the protrusion. Although this problem could be overcome by grinding the angled transition 203 to mirror the curved transition 103 of the inlay 100, this increases the time, cost and complexity of the manufacturing procedure. In addition, when the overlay 200 is made of ceramic material any grinding of the overlay could lead to chipping.

FIG. 1B shows an inlay 10 in accordance with the present invention. Here, grooves 14 are provided directly adjacent to and on either side of the protrusion 12 such that the protrusion 12 in effect begins within the circumference of the external circular symmetric surface 11. This removes the curved transition between the external surface 11 and the protrusion 12, or at least moves the location of this transition radially inward. The protrusion 12 now extends through the circular symmetric surface 11 rather than from this surface. Therefore, the overlay 200 can be placed over the inlay 10 and the protrusion 12 inserted into groove 202 without any interference between the inlay 10 and the angled transition area 203 of the overlay 200.

Thus, in accordance with the present invention a good, non-rotational connection can be obtained between the inlay and overlay without the need to modify the overlay.

The inlay can comprise a single protrusion, and thus two grooves. This is enough to secure the overlay against rotation relative to the inlay. However, for increased anti-rotational security it is preferable for the inlay to comprise a plurality of circumferentially spaced protrusions interposed by sections of circular symmetric external surface, the protrusions each being flanked by directly adjacent longitudinally extending grooves. Preferably the inlay comprises a plurality of identically shaped circumferentially spaced protrusions. As well as providing increased anti-rotational security, multiple identical protrusions also enable the overlay to be connected to the inlay in a number of different angular positions. In a particularly preferred embodiment the inlay comprises four identical protrusions spaced at 90° intervals about the longitudinal axis of the post portion. This is particularly beneficial when the overlay is not symmetrical about the longitudinal axis of the cavity, for example, the overlay comprises a coronal post portion extending along an axis at an angle to the longitudinal axis. Multiple identical protrusions enable the orientation of the angled coronal portion to be adjusted relative to the inlay.

The radial profile of the protrusion(s), i.e. the outline of the protrusion when viewed in a plane perpendicular to the longitudinal axis, can be any shape, for example rectangular, square, triangular etc. However, preferably the radial profile of the at least one protrusion comprises a curved distal surface. In other words the distal end of the protrusion is not pointed or flat but rounded. While the protrusion(s) can also comprise straight surfaces, e.g. planar lateral sides such that the protrusion has a "U" shaped cross section, it is preferred that the radial profile of the at least one protrusion is formed entirely of curved surfaces, e.g., the protrusion has a "C" shaped, arc-shaped or semi-circular cross section. This eases manufacturing and prevents the creation of sharp edges, which can be subject to high stresses during use of the inlay. Curved protrusions result in a better force distribution and reduce the likelihood of distortion.

In some embodiments the at least one protrusion may be tapered along all or a part of its length such that the protrusion has a greater radius at its apical end. Such a protrusion design can increase the security of the fit with the overlay by creating a force fit. However, it is preferable that the at least one protrusion has a substantially uniform maximum radius as measured from the longitudinal axis. Although it is possible for the radial profile of the at least one protrusion to alter along its length, for example the circumferential width of the protrusion may narrow in the coronal direction, the at least one protrusion preferably has a uniform radial profile along substantially the whole of its length as this simplifies the design of the corresponding overlay. By "substantially" it is meant excluding the extreme axial ends of the protrusion, which due to manufacturing constraints will usually comprise a slight taper, bevel or curved transition.

The longitudinally extending grooves directly border each protrusion. The radial profile of these grooves can have any shape, e.g. rectangular, square, triangular. However, it is preferred that the radial profile of each groove comprises a curved base surface. In other words, the floor of the groove is rounded. While the grooves can also comprise straight surfaces, e.g. planar lateral sides such that the grooves have a "U" shaped cross section, it is preferred that the radial profile of each groove is formed entirely of curved surfaces, e.g., the grooves have a "C" shaped, arc-shaped or semi-circular cross section. As with the protrusions, this eases manufacture and improves force distribution. For ease of manufacturing the grooves preferably have a substantially uniform mimimum radius as measured from the longitudinal axis and preferably a substantially uniform radial profile.

In accordance with the present invention the grooves are located directly adjacent to the protrusion(s). This means that there are no sections of external circular symmetric surface between the protrusion and its bordering grooves and instead the lateral sides of the protrusion join smoothly to the lateral sides of the grooves such that the protrusion extends into the body of the post portion. The side wall of the groove directly adjacent to the protrusion thus also forms the side wall of the proximal end of the protrusion.

According to a particularly preferred embodiment, the circumferential surfaces of the protrusion and its directly adjacent grooves are continuous, that is to say, the surfaces of the grooves and protrusion can be defined by a single unbroken curved wave function, having its maximum at the distal end of the protrusion and its mimima at the innermost point of the grooves. In such embodiments, the radial profile of both the protrusion and grooves are formed entirely of curved surfaces. Although the grooves themselves are curved, the transition between the grooves and the circular symmetric external surface of the post portion can be curved or sharp.

Preferably the grooves have a radial extension less than the radial extension of the at least one protrusion. In other words, the grooves extend into the inlay by a lesser extent than the protrusions extend outwards, as measured from the external circular symmetric surface. By keeping the grooves small their effect on the strength of the inlay is reduced. This is particularly important when the inlay comprises a through hole, for example so that a basal screw can be passed through the inlay to fasten this to the implant.

Preferably the at least one protrusion has a radial extension at least 50% greater than the radial extension of the grooves, more preferably an extension between 50-150% greater and most preferably a radial extension which is approximately twice the radial extension of the grooves.

Although the at least one protrusion can extend the length of the post portion, it is preferred that the one or more protrusion has a longitudinal length less than the length of the post portion, preferably less than half the length of the post portion, more preferably a length of between ¼ and ⅓ the length of the post portion. In a preferred embodiment the length of the protrusion is approximately 1 mm. Preferably the at least one protrusion is located in the apical most 50% of the post portion.

In order to improve the fit between the inlay and overlay, the grooves must extend the length of each protrusion. In a preferred embodiment the grooves extend substantially the length of the post portion of the inlay. This eases manufacture of the grooves and in addition the grooves can act as channels for a bonding material such as glue or cement. Such channels ensure the bonding material is distributed along the length of the post portion and also help to prevent or reduce the extrusion of bonding material at the interface between the inlay and overlay. Thus, the provision of longitudinal grooves extending the length of the post portion is beneficial even in embodiments in which the protrusions do not extend the full length of the post portion. According to one preferred embodiment therefore the longitudinally extending grooves have a longitudinal length greater than the protrusion which they border. Preferably the longitudinally extending grooves extend from the coronal end of the post portion to at least the apical end of the at least one protrusion.

The post portion comprises an external surface which is circular symmetric about the longitudinal axis. Thus the external surface can form a conical or frusto-conical shape. In such embodiments a protrusion having a uniform maximum radius will appear tapered in relation to the external surface. However, preferably the external surface is circular cylindrical.

The inlay is designed for connection to an implant. The shape of the connection geometry is dictated by the design of the implant to which it is intended to attach the inlay. The implant connection geometry can be designed to connect the inlay directly or indirectly to the implant. When used in two-part implant systems the inlay will most usually be designed for direct connection to the implant. However, in other multi-part systems an intermediate component, such as a collar or ring, may be positioned between the implant and the inlay such that the inlay connects to this intermediate part or to both the implant and the intermediate part. Regardless of whether the inlay connects directly or indirectly to the implant, this can be secured, i.e. axially fastened, to the implant system using a separate securing means, such as a screw or cement, or without such a means, e.g. through force or compression fitting, depending on designer choice. In other words, "indirectly/directly connected" to the implant refers only to whether the inlay directly contacts the implant and not to how the inlay is axially secured to the implant system.

As mentioned above, in one preferred embodiment the inlay comprises a through hole which extends from the coronal to apical end of the inlay. This enables a basal screw to be inserted through the inlay in order to fasten this directly or indirectly to the implant. Preferably the through hole comprises a reduction in diameter when viewed in the coronal to apical direction, thus forming a screw seat. However, as the inlay is intended for use with an overlay, in some embodiments the screw seat may be formed in the overlay and thus the through hole of the inlay can have a uniform diameter.

The connection geometry will usually comprise either a cavity for accommodating an axially protruding boss of the implant system or an apical portion for insertion into an internal bore. In a preferred embodiment the connection geometry comprises anti-rotation means for co-operation with implant system anti-rotation means. This could be, for example, a section of the cavity or apical portion having a polygonal cross-section or radially extending grooves or protrusions designed to complement a counterpart anti-rotation means on the implant system boss or internal bore respectively. Many such complementary anti-rotation means for multi-part implant systems are known in the art and any such known means can be employed with the inlay of the present invention.

In a particularly preferred embodiment, the implant connection geometry of the inlay comprises an apical portion for insertion into an internal bore of an implant. The apical portion preferably comprises an anti-rotation means for co-operation with an implant anti-rotation means. Preferably the apical portion further comprises, coronal of the anti-rotation means, a conical section which tapers radially inwards in the apical direction. The conical section enables an interference fit to be obtained with a complementary conical taper in the internal bore of the implant. This provides a tight seal between the inlay and implant and prevents incursion of bacteria into the implant.

Preferably the inlay further comprises, coronal of the implant connection geometry and apical of the post portion, a coronally facing platform. This platform provides an abutment surface on which the overlay can rest, thus forming an axial stop and support. The platform can extend radially in a plane perpendicular to the longitudinal axis of the post portion or at an angle to this, preferably an acute angle such that the platform tapers radially outwards in the coronal direction. This provides a secure stop which can withstand axial forces applied in the apical direction over the lifetime of the secondary component. This is particularly beneficial when the component is an abutment. In other embodiments the platform may taper outwards in the apical direction or take the form of a plurality of discontinuous, stepped surfaces, these surfaces being perpendicular or angled.

In such embodiments, the post portion extends coronally of the platform, the external circular symmetric surface of the post portion having a diameter less than the platform. Preferably the at least one protrusion also has a maximum radius less than the platform, such that the platform extends radially beyond the protrusion(s). Although the platform and post portion are often directly adjacent to each other, as both are designed in use to contact the overlay, it is possible for an intermediate portion to be formed between them. Similarly, the platform can be directly adjacent to or remote from the connection geometry, depending on design choice. The underside of the platform may, in certain embodiments, be designed to abut the coronal end of the implant. This can assist in sealing the implant against bacterial incursion.

Although the at least one protrusion could be located directly adjacent to the coronally facing platform, it is preferred for the at least one protrusion to be axially spaced from the platform. This eases production of the inlay, as it enables the platform to be created by turning. This ensures an even, smooth finish and thus a flush fit between the platform and the overlay.

Preferably the protrusions are spaced from the platform by a distance of at least 0.25 mm, preferably by a distance of less then 1.25 m. In a particularly preferred embodiment the at least one protrusion is spaced by a distance of approximately 0.5 mm from the platform. Viewed in an alternative manner, the at least one protrusion is preferably located in the coronal most 90% of the post portion. Thus, even when the post portion is directly adjacent to the coronally facing platform the at least one protrusion is axially spaced from this platform. Further, the at least one protrusion can be located within the apical most 50% of the post portion. In other words, in a particularly preferred embodiment the protrusion is not located within the coronal most half of the post portion or the apical most 10%.

In preferred embodiments the post portion may comprise, in addition to the longitudinally extending grooves, at least one circumferentially extending groove. This groove may extend only partly around the circumference of the post portion, and in such instances two or more circumferentially extending grooves may be located at the same axial location, thus forming a "broken" or "dashed" groove. However, preferably the at least one circumferentially extending groove extends about the whole circumference of the post portion. Preferably a plurality of axially spaced circumferentially extending grooves is provided. The circumferentially extending grooves provide channels for bonding material, which together with the longitudinal grooves can help to ensure an even distribution of bonding material over the length and circumference of the post portion.

Although the circumferentially extending grooves may dissect the one or more protrusion, in effect creating two axially spaced protrusions, it is preferable that the one or more circumferentially extending groove is located remote from the at least one protrusion. The circumferentially extending groove could be located angularly remote from the at least one protrusion, i.e., the circumferentially extending groove does not extend about the entire circumference of the post portion but is "dashed" or "broken" such that it does not traverse the at least one protrusion. Preferably however the at least one circumferentially extending groove is located axially remote from the at least one protrusion, preferably in the coronal direction.

In some embodiments a circumferentially extending groove can be located directly adjacent to the coronal end of the at least one protrusion. In this manner, the groove can enable the coronal end surface of the protrusion to extend into the post portion, thus preventing a curved transition between this end and the circular symmetric external surface of the post portion. This can be beneficial when the longitudinal length of the at least one groove of the overlay is similar to that of the protrusion, as the circumferential groove will prevent any interference between the coronal-end transitional areas of the overlay groove and inlay protrusion, in the same manner as discussed above in relation to the longitudinally extending grooves and lateral side transitions. However, in most instances, the overlay grooves will have a longer length than the protrusions they are designed to accommodate. This is possible as the protrusions of the inlay and grooves of the overlay are only intended to prevent rotational play, hence it is only the lateral dimensions of these features which must be closely matched. Therefore, a directly adjacent circumferential groove is not an essential feature of the present invention.

Preferably the circumferentially extending groove or grooves have the same depth and profile, for example curved, as the longitudinal grooves. In other embodiments however the circumferential grooves may be shaped so as to form undercuts, such that the intervening segments of post portion have apically facing crests. Such crests can resist the removal of the overlay once this has been placed over the inlay.

The circumferentially extending groove or grooves may also extend in the axial direction, such that the grooves have a helical shape. However, preferably each circumferentially extending groove is located in a plane perpendicular to the longitudinal axis of the inlay.

The inlay of the present invention is intended for use with an overlay comprising an apical accommodation cavity for housing the post portion of the inlay, the accommodation cavity extending along a longitudinal axis and comprising a circular symmetric cavity wall, which is complementary to the circular symmetric external surface of the post portion, and at least one groove. The accommodation cavity and at least one groove are dimensioned to enable the overlay to be positioned over the inlay such that the one or more protrusion of the post portion is housed in the one or more groove of the overlay in order to inhibit relative rotation between the components. As discussed above, the design of the inlay prevents any interference between the lateral transitions from the cavity wall to the groove of the overlay with the lateral transitions from the external surface to the protrusion of the inlay. This leads to a better fit between the components.

Aside from the at least one groove, arranged in use to house the at least one protrusion of the inlay, the circular symmetric cavity wall is preferably unbroken. In other words, the accommodation cavity consists only of the circular symmetric cavity wall and at least one protrusion. More generally, the accommodation cavity does not comprise any protrusions arranged for insertion into the longitudinally extending grooves of the inlay or, where present, the circumferentially extending grooves. These grooves of the inlay are purposely included in order to create discrepancies between the geometry of the inlay and overlay such that, firstly, a better rotational locking between the components can be obtained and secondly, to provide channels for good distribution of glue or cement.

Together the inlay and overlay form a hybrid secondary component for attachment to an implant. The inlay is designed to provide the connection to the implant while the overlay enables the functional part of the component to be formed of a different material to the inlay.

According to a further aspect the present invention therefore provides a hybrid secondary component, comprising an inlay for connection to a dental implant and an overlay, the inlay comprising implant connection geometry, for connecting the component to the implant and, coronal of the implant connection geometry, a post portion extending along a longitudinal axis, the post portion having a circular symmetric external surface and comprising at least one protrusion extending radially beyond said external surface, wherein the post portion further comprises longitudinally extending grooves which extend radially inward of said external surface and are located directly adjacent to and on either side of the at least one protrusion such that the proximal end of said at least one protrusion is located radially inward of said external surface, the overlay comprising an apical accommodation cavity for housing the post portion of the inlay, the accommodation cavity extending along a longitudinal axis and comprising a circular symmetric cavity wall, which is complementary to the circular symmetric external surface of the post portion, and at least one groove dimensioned such that the one or more protrusion of the inlay can be housed in the one or more groove of the overlay in order to inhibit relative rotation between the components.

The inlay may comprise any of the above described preferred features, alone or in combination.

In a preferred embodiment the accommodation cavity comprises a plurality of identical circumferentially spaced grooves interposed between sections of circular symmetric cavity wall for housing a plurality of identical inlay protrusions.

Preferably the inlay and overlay are bonded together although it is also possible for other connection methods to be used, for example the overlay may be pressed onto the inlay.

In preferred embodiments the inlay is a metal component, most preferably titanium or titanium alloy, such as TAN. The overlay is preferably formed of a non metallic material, for example ceramic or polymer. Particularly preferred materials for the overlay are zirconium dioxide (zirconia), silicon dioxide, PEEK and PMMA.

It is preferred, particularly in embodiments in which the inlay and implant are made of metal and the overlay of a non-metal, that the inlay provides the sole contact between the hybrid secondary component and the implant. This prevents any damage to the implant or overlay caused by contact between materials of differing hardness. In such embodiments therefore, the overlay is fixed to the inlay at location coronal of the implant connection geometry. In preferred embodiments the apical end of the overlay abuts the coronally facing platform of the inlay such that all areas of the inlay coronal of the platform are surrounded by the overlay and all areas apical of the platform are exposed.

The hybrid secondary component can be used, for example, as a healing cap. In such embodiments the outer surface of the overlay is shaped to protrude into, and in some cases just over, the gingiva and create a natural emergence profile; that is, the external shape of the overlay mimics the external shape of the transgingival portion of a tooth. This enables the gingiva to heal around the healing cap in a shape that will allow a realistically shaped prosthesis to be attached to the implant at a later time. In other embodiments the secondary component may form a part of the multi-part implant, for example an intermediate part such as a collar.

In a preferred embodiment the hybrid secondary component is an abutment. In such embodiments the overlay comprises a coronal abutment post portion for providing core support to a dental prosthesis. The abutment post portion of the overlay may be co-axial with the longitudinal axis of the accommodation cavity or it may extend at an angle to this.

In certain embodiments the overlay will further comprise a shoulder apical of the abutment post portion which forms a platform against which the prosthesis can abut. More generally the external shape of the overlay can take the form of any abutment shape known in the art. The sole requirement is that the abutment shape is capable of supporting a prosthesis which can be glued, cemented, screwed or directly veneered to the abutment. In some embodiments the abutment itself may form the dental prosthesis, that is to say, the exterior of the overlay is shaped to replicate a human tooth or teeth. In these embodiments the prosthesis is integrally formed with the core support of the abutment.

The post portion of the inlay can have a length substantially equal to the length of the overlay, such that the post portion extends the full length of the overlay. However, in many embodiments the post portion has a length less then the overlay such that the overlay extends coronally above the inlay. In this way the colour of the coronal areas of the overlay are not influenced by the inlay colouring.

The accommodation cavity of the overlay can form a blind bore. In such instances the secondary component must either be connected to the implant by bonding, force fit etc or the inlay must be screwed to the implant prior to attachment of the overlay.

In preferred embodiments however both the overlay and inlay comprise a through hole, the through hole of the overlay comprising, at its apical end, the accommodation cavity. This enables the overlay to be bonded to the inlay and afterwards for the hybrid component to be attached to the implant via a basal screw. In such embodiments the through hole of the overlay must, in use, communicate with the through hole of the inlay. Preferably these two through holes are, when the inlay and overlay are connected together, coaxial with one another. In any event, and in all embodiments, the longitudinal axes of the post portion and accommodation cavity are, in use, co-axial in order to enable the post portion to be snugly housed in the cavity.

Preferably the external shape of the overlay is individualised, that is to say, the exterior of the overlay is designed for use with a specific patient.

According to a further aspect the present invention provides a method of forming a dental abutment comprising the steps of providing an inlay in accordance with the present invention; creating, using computer software, a virtual overlay with an individualised exterior and a standardised accommodation cavity in order to enable connection to the inlay; creating a physical overlay in accordance with the virtual overlay; and bonding the overlay to the inlay.

The benefits of the invention herebefore described can also be achieved with a hybrid secondary component in which the accommodation cavity of the overlay comprises at least one protrusion and directly adjacent longitudinally extending grooves. Such an overlay can be used with an inlay having a post portion comprising at least one groove shaped to house the at least one protrusion.

Thus, in accordance with a further aspect, the present invention provides an overlay for connection to an inlay, comprising an accommodation cavity, for housing at least a portion of the inlay, the accommodation cavity comprising a circular symmetric cavity wall and at least one protrusion extending radially inward of said cavity wall into said cavity, wherein the accommodation cavity further comprises longitudinally extending grooves which extend radially beyond said cavity wall into said overlay and are located directly adjacent to and on either side of the at least one protrusion such that the proximal end of said at least one protrusion is located radially beyond said cavity wall.

Viewed from a further aspect the present invention provides a hybrid secondary component comprising an inlay for connection to a dental implant and an overlay, the inlay comprising implant connection geometry, for connecting the component to the implant and, coronal of the implant connection geometry, a post portion extending along a longitudinal axis, the post portion having a circular symmetric external surface and comprising at least one groove extending radially inward of said external surface, the overlay comprising an apical accommodation cavity for housing the post portion of the inlay, the accommodation cavity extending along a longitudinal axis and comprising a circular symmetric cavity wall, which is complementary to the circular symmetric external surface of the post portion, and at least one protrusion extending radially inwards of said cavity wall into said cavity and dimensioned such that the one or more protrusion of the overlay can be housed in the one or more groove of the inlay in order to inhibit relative rotation between the components, the overlay further comprising longitudinally extending grooves which extend radially beyond said cavity wall into said overlay and are located directly adjacent to and on either side of the at least one protrusion such that the proximal end of said at least one protrusion is located radially beyond said cavity wall.

In such embodiments the preferred features of the post portion of the inlay as discussed in detail above are instead preferably features of the accommodation cavity, adapted where necessary to take account of the inverted geometry. Conversely, the preferred features of the overlay as discussed in detail above are instead preferably features of the post portion. This inversed aspect of the invention can be particularly beneficial when the overlay is formed of metal or plastics, which are easier to shape than ceramics.

Preferred aspects of the present invention shall now be described, by way of example only, with reference to the accompanying drawings, in which.

BRIEF DESCRIPTION OF THE DRAWINGS

DETAILED DESCRIPTION OF THE INVENTION

Figure 2:
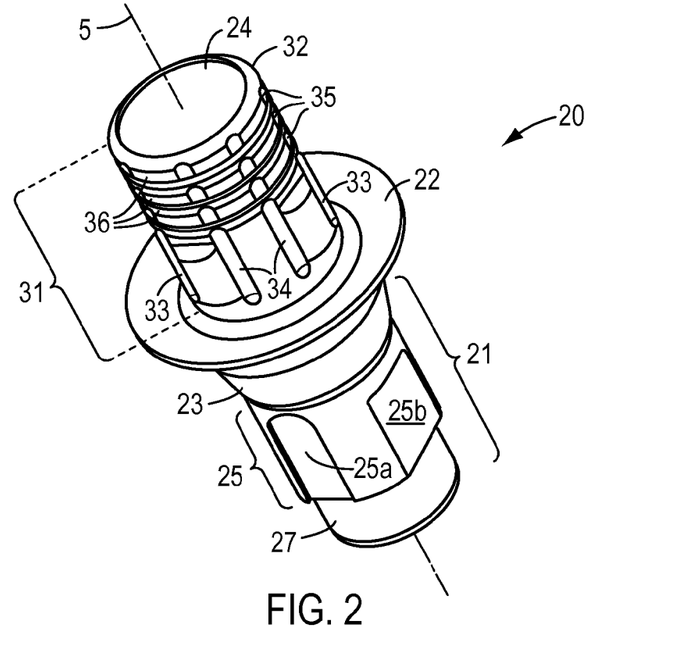
FIG. 2 shows a perspective view of an inlay in accordance with the present invention.

FIG. 2 shows an inlay 20 in accordance with the present invention. It comprises apical portion 21 having implant connection geometry. The apical portion 21 is shaped for insertion into an internal bore of a dental implant. Apical portion 21 comprises a conical portion 23 tapering in the apical direction and, apical of conical portion 23, anti-rotation means 25. In the present embodiment anti-rotation means 25 comprises a series of grooves 25a and flats 25b. These are positioned and dimensioned to co-operate with a number of protrusions within the bore of the implant, such that the inlay 20 is held in a rotationally locked position relative to the implant. Apical portion 21 further comprises, apical of the anti-rotation means 25, circular cylindrical guidance portion 27 which helps to centre the inlay 20 during insertion into the implant.

Coronal of the apical portion 21, the inlay 20 comprises a coronally facing platform 22 which acts as an abutment surface and axial stop for the overlay. In this embodiment the platform 22 is at an acute angle to the longitudinal axis 5, which means the platform 22 tapers outwards in the coronal direction. In other embodiments however the platform will be perpendicular to the longitudinal axis.

Post portion 31 extends coronally from platform 22 along longitudinal axis 5. The post comprises a circular cylindrical external surface 32 which is circular symmetrical about axis 5. Protruding radially outwards beyond this surface 32 are four protrusions 33, which are interposed by sections of the circular cylindrical surface 32. These protrusions 33 form a second anti-rotation means which enables the inlay to be connected in a non-rotational manner to an overlay.

In accordance with the present invention, longitudinally extending grooves 34 are provided directly adjacent to and on each lateral side of the protrusions 33. These grooves 34 have the effect that the protrusions extend radially inwards of the circular symmetric external surface 32 and thus prevent a curved transition occurring at this surface 32.

The benefits afforded by this "insetting" of the protrusions 33 are described above with reference to FIGS. 1A and 1B.

In this embodiment grooves 34 extend the length of post portion 31, in order to assist with an even distribution of bonding material.

The protrusions 33 are located in the apical most half of the post portion 31, however, these are axially remote from the platform 22. This assists with the manufacture of the platform 22.

Coronal of the protrusions 33 post portion 31 comprises a series of circumferentially extending grooves 35. Each groove 35 extends around the full circumference of the post portion 31 and is located in a plane perpendicular to the longitudinal axis 5. The grooves 35 are axially spaced, such that ribs 36 are formed between them. Such circumferentially extending grooves 35 further assist with the distribution of bonding material.

Inlay 20 comprises a through hole 24 to enable a basal screw to be inserted in order to fasten the inlay 20 to an implant.

Figure 3:
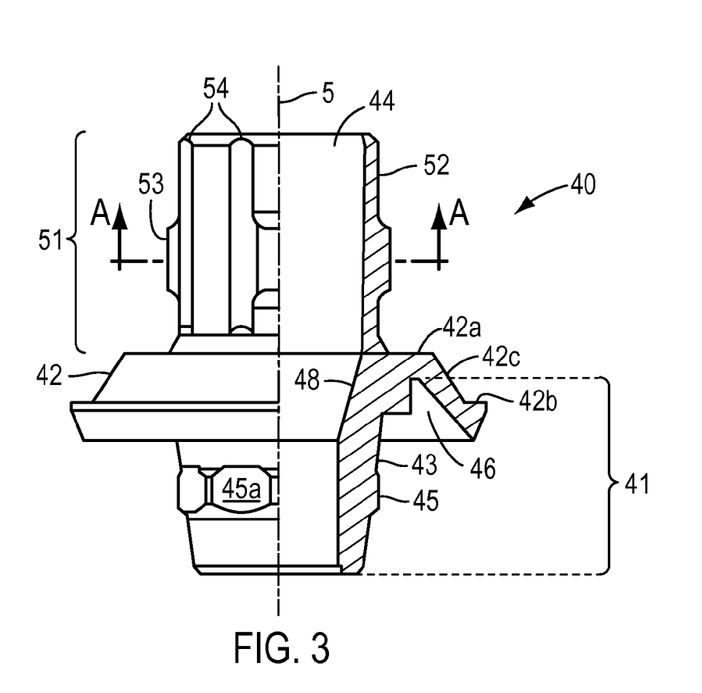
FIG. 3 shows a partial cross-section through an inlay in accordance with a second embodiment of the present invention.

FIG. 3 shows a partial cross-section through another inlay 40 in accordance with the present invention. Here, once again the inlay comprises an apical portion 41 having a tapered conical section 43 and anti-rotation means 45. In this embodiment anti-rotation means 45 consists of a number of flat sides 45a which form an octagonal cross section. The inlay can thus be inserted into an implant bore having a complementary octagonal cross section to fix the inlay in an anti-rotational manner.

Inlay 40 also comprises a coronally facing platform 42. In this embodiment the underside 46 of the platform 42 is shaped to fit over a downwardly extending coronal surface of the implant, thus sealing the implant bore. Platform 42 forms two planar stepped abutment surfaces 42a, 42b and a sloped abutment surface 42c, each or all of which can be abutted by the overlay. It is preferred that the overlay is designed to abut at least planar abutment surface 42b, as this best seals the hybrid component and prevents microgaps.

Post portion 51 extends coronally from shoulder 42 along longitudinal axis 5. In the same manner as FIG. 2 the post portion 51 comprises four evenly circumferentially spaced protrusions 53 bordered on either side by longitudinally extending grooves 54 such that the protrusions extend radially inwards of circular cylindrical external surface 52. The protrusions 53 have a substantially uniform radius and profile along their length. Once again grooves 54 extend along the length of post portion 51 and protrusions 53 are axially spaced from the platform 42. However, in this embodiment post portion 51 does not comprise circumferentially extending grooves.

Once again the inlay 40 comprises an axially extending through hole 44. As can be seen from the partial cross-section, through hole 44 comprises a reduction in diameter in the coronal to apical direction which forms a screw seat 48.

Figure 4:
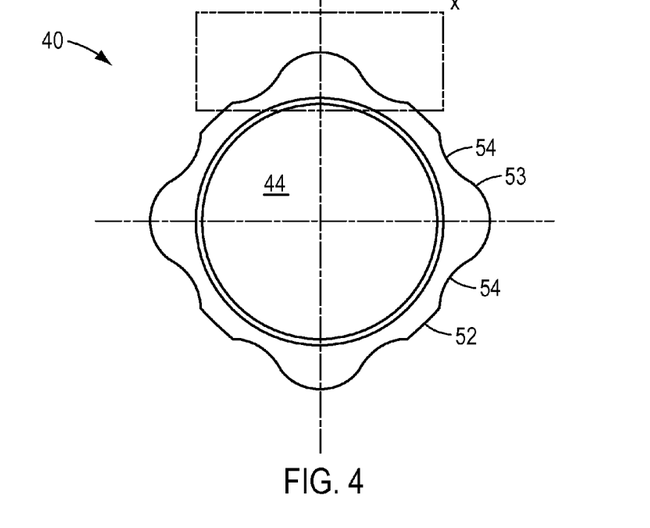
FIG. 4 shows a cross section along line A-A of FIG. 3.

FIG. 4 shows a cross-section through the protrusions 53 of FIG. 3, however this cross-section is equally applicable to the inlay of FIG. 2.

Here it can be clearly seen that the grooves 54 extend radially inwards of circular symmetric surface 52 while protrusions 53 extend radially beyond this surface. The placement of grooves 54 directly adjacent to each protrusion 53 acts to effectively extend these protrusions radially inwards of the external surface 52 such that they are inset.

In this embodiment, the circumferential surfaces of the protrusions 53 and its bordering grooves 54 are curved and form a continuous wave-like surface. The maximum of the curved wave function is formed at the distal end of the protrusion 53 and its minima at the innermost point of the grooves 54. This can best be seen in FIG. 5. The curved nature of the surfaces helps to evenly distribute the forces experienced by the inlay and thus prevents damage of the component.

Figure 5:
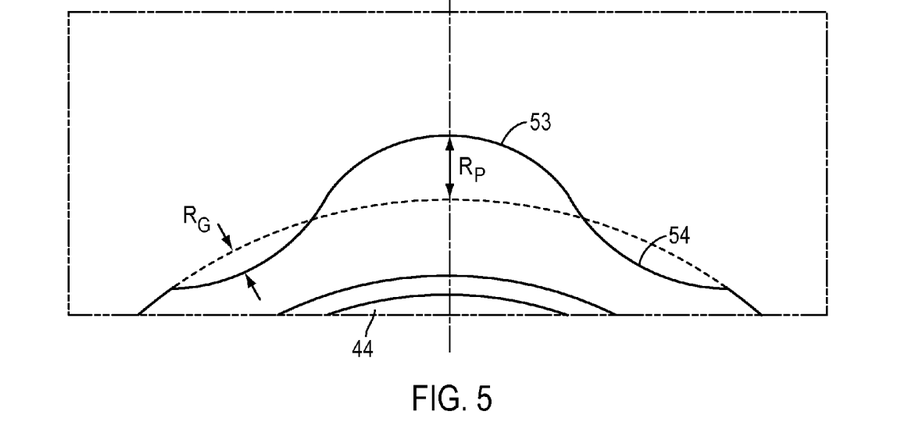
FIG. 5 shows detail X of FIG. 4.

As can also be seen from FIG. 5, the radial extension $R_G$ of the grooves 54 into the post portion 51 is less than the radial extension $R_P$ of the protrusions 53 outwards, as measured from the circular symmetric surface 52 (shown in dotted lines). This prevents weakening of the post portion and also prevents the grooves 54 from interfering with through hole 44.

Figure 6:
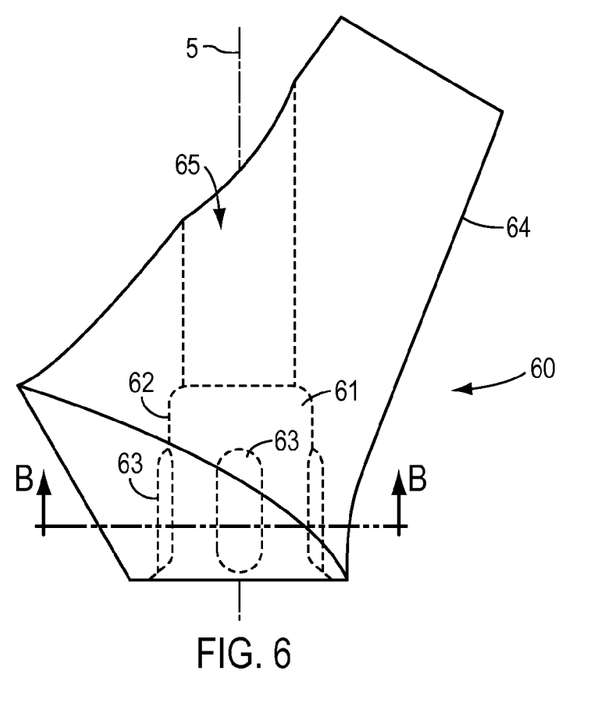
FIG. 6 shows a lateral view of an overlay suitable for use with an inlay in accordance with the present invention.
Figure 7:
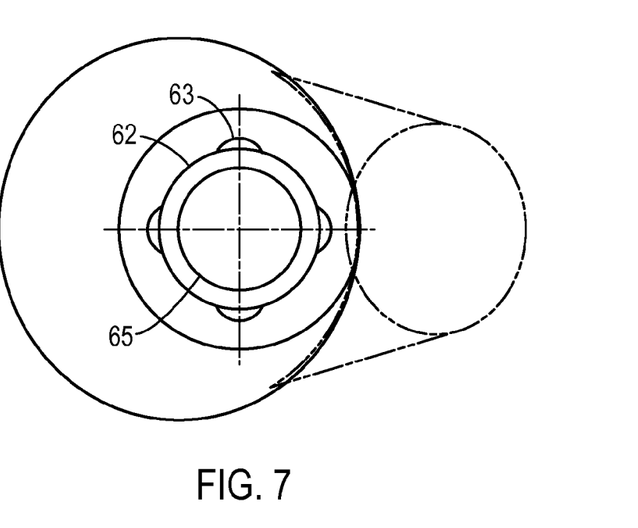
FIG. 7 shows a cross-section along line B-B of FIG. 6.

FIGS. 6 and 7 show an overlay 60 for use with an inlay in accordance with the present invention. Overlay 60 comprises accommodation cavity 61 at its apical end. Cavity 61 is formed of circular cylindrical cavity wall 62 from which radially extending grooves 63 extend into the overlay. Circular cylindrical wall 62 is dimensioned to complement circular cylindrical external surface 32, 52 such that the inlay fits snugly within the accommodation cavity 61. Grooves 63 are arranged evenly circumferentially spaced about the longitudinal axis 5 of the cavity 61 and are shaped to accommodate protrusions 33, 53 of the inlay. As can be seen from FIG. 7, sharp edges are formed at the transition between the cavity wall 62 and protrusions 63. However, as demonstrated by FIG. 1B, the longitudinal grooves 34, 54 of the inlay prevent any jamming or rotational play caused by these sharp edges.

Abutment post portion 64 extends at an angle to longitudinal axis 5, thus forming an angled abutment. It is the abutment post portion 64 which will provide core support to the prosthesis in use. Through hole 65 enables a basal screw to be inserted through overlay 60.

Figure 8:
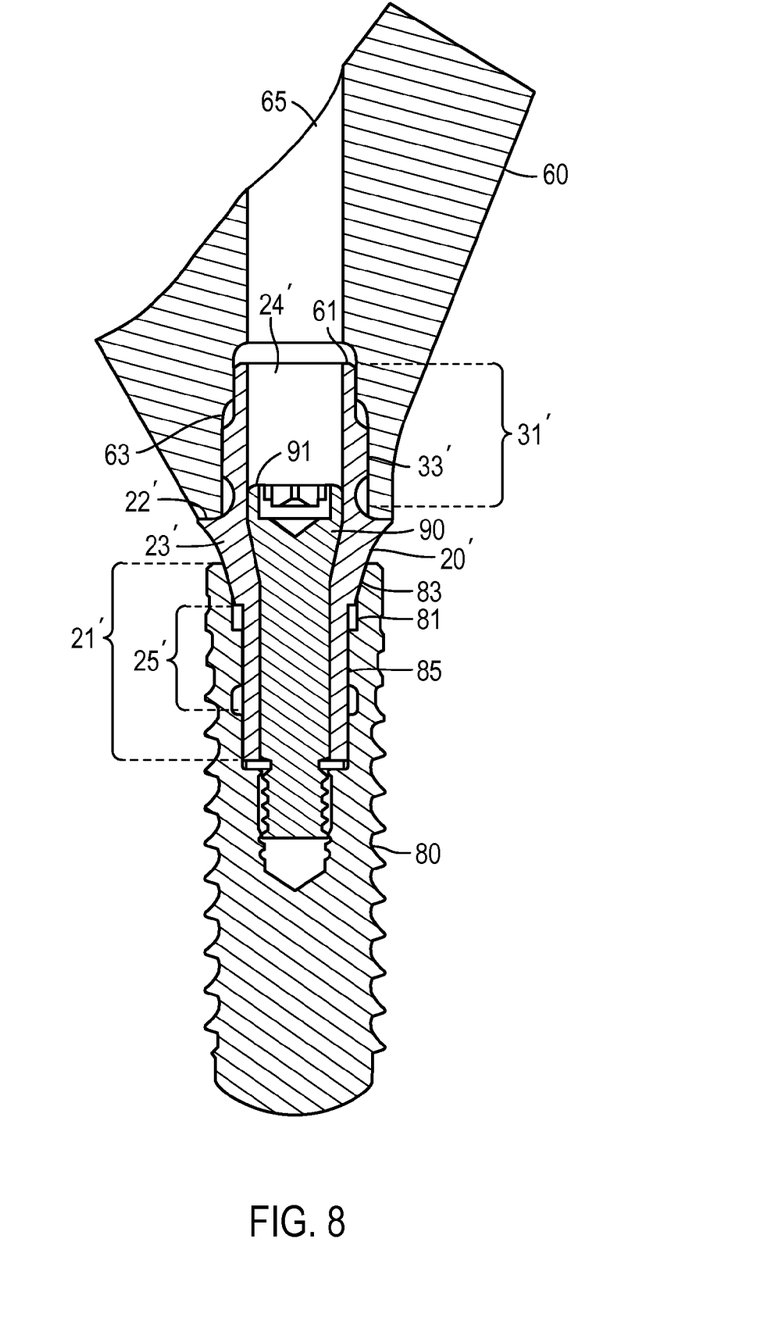
FIG. 8 shows a cross section through an assembly of an implant and a hybrid abutment in accordance with the present invention.

FIG. 8 shows a cross-section through a hybrid secondary component according to the present invention, consisting of overlay 60 attached to inlay 20', which is identical to that of FIG. 2 except that platform 22' is perpendicular rather than acutely angled. This hybrid secondary component is shown attached to implant 80. Here it can be seen that apical portion 21' fits into internal bore 81 of the implant.

This internal bore 81 comprises a conical section 83, for forming a tight seal with conical portion 23' of the inlay 20', and anti-rotation means 85 which co-operates with anti-rotation means 25' to rotationally fix the inlay 20' relative to the implant 80.

Overlay 60 is bonded to inlay 20' using suitable bonding material such as cement. Post portion 31' is housed within accommodation cavity 61, with protrusions 33' fitting within grooves 63. Through holes 24', 65 align to create a screw channel for insertion of basal screw 90. Screw head 91 abuts against the screw seat of the inlay to fasten the hybrid component to the implant 80. As can be clearly seen in this figure, overlay 60 is not in contact with implant 80 and instead the connection between implant 80 and abutment is metal to metal. The same advantage can be achieved with many different configurations of hybrid secondary component, particularly those wherein the inlay has a platform on which the overlay abuts and which is coronal of the connection geometry.

The external shape of the overlay 60 can be pre-configured in a standard shape or it may be individualised according to the specific oral situation of the patient. The invention is thus not limited to any particular exterior shape of the overlay.

The above described embodiments are for illustrative purposes only and the skilled man will realize that many alternative arrangements are possible which fall within the scope of the claims. In particular, the inlay may comprise alternative implant connection geometry, such as a cavity for connection to an implant boss. In such embodiments the implant connection cavity may axially overlap the post portion. Further, in the above described embodiments the inlay comprises four protrusions with curved surfaces. In other embodiments different shapes and numbers of protrusions can be used.

Where technical features mentioned in any claim are followed by reference signs, those reference signs have been included for the sole purpose of increasing intelligibility of the claims and accordingly, such reference signs do not have any limiting effect on the scope of each element identified by way of example by such reference signs.

The invention claimed is:

1. An inlay (20) for connection to a dental implant (80), comprising
    implant connection geometry, for connecting the inlay to the implant and, coronal of the implant connection geometry,
    a post portion (31) extending along a longitudinal axis, the post portion having a circular symmetric external surface (32) and comprising at least one protrusion (33) extending radially beyond said external surface, wherein the post portion further comprises longitudinally extending grooves (34) which extend radially inward of said external surface and are located directly adjacent to and on either side of the at least one protrusion such that the proximal end of said at least one protrusion is located radially inward of said external surface.

2. An inlay (20) as claimed in claim 1, wherein the inlay comprises a plurality of circumferentially spaced protrusions (33) interposed by sections of circular symmetric external surface (32), each protrusion being flanked by directly adjacent longitudinally extending grooves (34).

3. An inlay (20) as claimed in claim 1 wherein a radial profile of the at least one protrusion (33) comprises a curved distal surface.

4. An inlay (20) as claimed in claim 3 wherein the radial profile of the at least one protrusion (33) is formed entirely of curved surfaces.

5. An inlay (20) as claimed in claim 1, wherein a radial profile of each longitudinally extending groove (34) comprises a curved base surface.

6. An inlay (20) as claimed in claim 5 wherein the radial profile of each longitudinally extending groove (34) is formed entirely of curved surfaces.

7. An inlay (20) as claimed in claim 1, wherein a circumferential surfaces of the at least one protrusion (33) and its directly adjacent grooves (34) are continuous.

8. An inlay (20) as claimed in claim 1, wherein the longitudinally extending grooves (34) have a radial extension less than the radial extension of the at least one protrusion (33), as measured from the circular symmetric external surface (32).

9. An inlay (20) as claimed in claim 8, wherein the at least one protrusion (33) has a radial extension at least 50% greater than the radial extension of the grooves (34).

10. An inlay (20) as claimed in claim 1 wherein the longitudinally extending grooves (34) extend substantially the length of the post portion (31).

11. An inlay (20) as claimed in claim 1, wherein the at least one protrusion (33) has a longitudinal length less than the length of the post portion (31).

12. An inlay (20) as claimed in claim 1 wherein the circular symmetric external surface (32) is circular cylindrical.

13. An inlay (20) as claimed in claim 1 wherein the inlay comprises a through hole (24) which extends from the coronal to apical end of the inlay.

14. An inlay (20) as claimed in claim 1 wherein the inlay further comprises, coronal of the implant connection geometry and apical of the post portion (31), a coronally facing platform (22).

15. An inlay (20) as claimed in claim 14, wherein the at least one protrusion (33) is axially spaced from the platform (22).

16. An inlay (20) as claimed in claim 1, wherein the post portion (31) comprises at least one circumferentially extending groove (35).

17. An inlay (20) as claimed in claim 1 in combination with an overlay (60), the overlay comprising
    an apical accommodation cavity (61) for housing the post portion (31) of the inlay, the accommodation cavity extending along a longitudinal axis and comprising a circular symmetric cavity wall (62), which is complementary to the circular symmetric external surface (32) of the post portion, and at least one groove (63),
    the accommodation cavity and at least one groove being dimensioned to enable the overlay to be positioned over the inlay such that the at least one protrusion (33) of the post portion is housed in the at least one groove of the overlay in order to inhibit relative rotation between the components.

18. A combination as claimed in claim 17 wherein the circular symmetric cavity wall (62) is unbroken aside from the at least one groove (63), such that the accommodation cavity consists only of the circular symmetric cavity wall and at least one groove.

19. A hybrid secondary component, comprising
    an inlay (20) for connection to a dental implant (80) and an overlay (60), the inlay comprising
    implant connection geometry, for connecting the component to the implant and, coronal of the implant connection geometry,
    a post portion (31) extending along a longitudinal axis (5), the post portion having a circular symmetric external surface (32) and comprising at least one protrusion (33) extending radially beyond said external surface, wherein the post portion further comprises longitudinally extending grooves (34) which extend radially inward of said external surface and are located directly adjacent to and on either side of the at least one protrusion such that the proximal end of said at least one protrusion is located radially inward of said external surface, the overlay comprising an apical accommodation cavity (61) for housing the post portion of the inlay, the accommodation cavity extending along a longitudinal axis and comprising a circular symmetric cavity wall (62), which is complementary to the circular symmetric external surface of the post portion, and at least one groove (63) dimensioned such that the one or more protrusion of the inlay can be housed in the one or more groove of the overlay in order to inhibit relative rotation between the components.

20. A hybrid secondary component as claimed in claim 19 wherein the circular symmetric cavity wall (62) is unbroken aside from the at least one groove (63), such that the accommodation cavity consists only of the circular symmetric cavity wall and at least one groove.

21. A hybrid secondary component as claimed in claim 19 wherein the hybrid secondary component is an abutment.

22. A hybrid secondary component as claimed in claim 19 wherein the inlay (20) is formed of metal chosen from titanium and titanium alloy, and the overlay (60) is formed of a non metallic material chosen from ceramic and polymer.

\* \* \* \* \*